United States Patent [19]

Nikolaiski

[11] 4,217,445
[45] Aug. 12, 1980

[54] 5-OXY-SUBSTITUTED DERIVATIVES OF PSORALENE USEFUL IN DERMATOLOGY

[75] Inventor: Eckhard Nikolaiski, Räterschen, Switzerland

[73] Assignee: Fotobio Holding AG, Zug, Switzerland

[21] Appl. No.: 800,782

[22] Filed: May 26, 1977

[30] Foreign Application Priority Data

May 28, 1976 [CH] Switzerland ............... 6688/76

[51] Int. Cl.$^2$ ............ C07H 17/06; C07D 493/04
[52] U.S. Cl. ..................... 536/4; 260/343.21; 549/71; 424/203; 424/180; 424/275; 424/279
[58] Field of Search ............ 260/343.21, 343.44, 260/332.2 C, 287 XA, 287 H; 560/130, 108; 536/4

[56] References Cited

U.S. PATENT DOCUMENTS

| | | | |
|---|---|---|---|
| 2,345,635 | 4/1944 | Stahmann | 260/343.44 |
| 2,889,337 | 6/1959 | Stanley et al. | 260/343.44 |
| 3,201,421 | 8/1965 | Kaufman | 260/613 R |
| 3,244,729 | 4/1966 | Eymard | 260/343.21 |
| 3,553,236 | 1/1971 | Hascher | 260/343.21 |
| 3,985,896 | 10/1976 | Brenner et al. | 260/346.22 |

OTHER PUBLICATIONS

Fieser & Fieser, (I) Reagents for Organic Synthesis, vol. 1, p. 964.
Fieser & Fieser, (II) Reagents for Organic Synthesis, vol. 4, p. 452.
Wagner et al., Wiley & Sons, Inc. N.Y., 1953, pp. 481-482.
Rodighiero et al., Chem. Abstracts, vol. 50 10091i.
Bohlmann et al., Chem. Abstracts, vol. 83 1975 206139z.
Ghoshal et al., Chem. Abstracts, vol. 59 1963, 11459c.

Primary Examiner—Henry R. Jiles
Assistant Examiner—Jane T. Fan
Attorney, Agent, or Firm—Frishauf, Holtz, Goodman & Woodward

[57] ABSTRACT

An improved process for obtaining 5-methoxy-psoralene from bergamot oil, a method for preparing the compound 5-hydroxy-psoralene from 5-methoxy-psoralene and a method of making novel psoralene derivatives by replacing the hydrogen atom of the 5-hydroxy group with an R group are disclosed. These compounds are prepared by reacting the 5-hydroxy-psoralene with a halide RX in the presence of sodium hydride. Compounds of particular interest are those of which the radical R is: alkanoyl of not more than 10 carbon atoms; orthoacetoxy-benzoyl; αthenoyl; O,O diethyl-phosphono; diethylaminoethyl, and 2'3'4'6' tetra α acetyl D-gluco pyranosyl.

8 Claims, No Drawings

5-OXY-SUBSTITUTED DERIVATIVES OF PSORALENE USEFUL IN DERMATOLOGY

The present invention relates to an improved method for making 5-methoxy-psoralene and 5-hydroxypsoralene, and novel derivatives of psoralene and their preparation. The formula of these new compounds is:

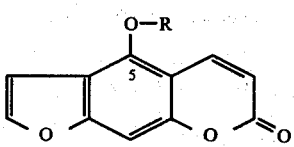

in which R is a hydrogen atom or an acylated aliphatic, aromatic, hetrocyclic, phosphorylated, alkylated or amino-alkylated group.

5-Methoxy-psoralene (also known as bergaptene) of formula:

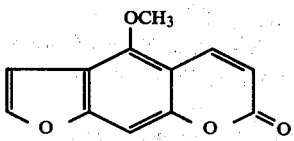

is known and is used in dermatology, particularly in the treatment of leucodermia and psoriasis.

Bergaptene is conventionally isolated from bergamot oil by cooling between $-10°$ and $-20°$ C. and recrystallising the oily precipitate in hot absolute ethanol.

Bergaptene can also be extracted from the wax obtained by low temperature ageing of bergamot oil. Extraction is also effected by means of ethanol with an average yield of 30 to 33% bergaptene.

These processes are extremely onerous due to the high price of absolute ethanol and the handling of large quantities thereof in the hot state.

The first object of the invention is an economic process for the extraction of bergaptene which is compatible with the treatment of large quantities thereof.

Another object of the present invention is a process for producing 5-hydroxy-psoralene.

It is also an object of the present invention to provide novel psoralene derivatives and a process for producing them.

SUMMARY OF THE INVENTION

The process for producing bergaptene which comprises aging bergamot oil by storing in a cold atmosphere at below $0°$ C. for several months, thus obtaining a wax constituted by a paste-oil mixture, suction-filtering said wax with a vacuum pump, compressing (that is pressing or squeezing) it to eliminate most of the oil and then washing the cake at least twice with its volume of a suitable non-polar solvent such as ligroin, pentane or light petroleum, or any other compatible non-polar solvent, followed by draining and suction-filtering accompanied by careful compressing, to produce the product as set forth in Example 1.

The 5-methoxypsoralene prepared in this way is used for the synthesis of 5-hydroxy-psoralene (also known as bergaptol) which is the starting substance for the preparation of the other psoralene derivatives according to the invention.

5-Hydroxy-psoralene has already been described and isolated. A synthesis process by the demethylation of 5-methoxy-psoralene by anhydrous pyridinium chloride is preferred for the purposes of the present invention.

The following are examples of the various demethylation agents which have been tested: Lewis acids, hydrogen halides of different concentrations, diborane in the presence of iodine, lithium iodide, and alkaline glycolates. Only pyridinium chloride led to a hydroxylated derivative with a yield above 80%, as illustrated in Example 2. It is prepared by the demethylation of 5-methoxy-psoralene by reacting with anhydrous pyridinium chloride at a temperature of $170°$ to $190°$ C. accompanied by constant agitation for one to four hours, treating with crushed ice and washing the mixture obtained several times with cold water, drying and recrystallising the 5-hydroxy-psoralene in absolute ethanol.

The present invention provides novel psoralene derivatives of formula:

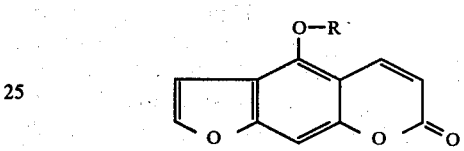

in which R is an acyl radical other than formyl having an aliphatic carbon chain of not more than 10 carbon atoms, ortho-acetoxy-benzoyl, α thenoyl, O,O diethylphosphono, di-alkyl-amino-alkyl in which each alkyl group has not more than a few carbon atoms, and $2'3'4'6'$ tetra α acetyl D-gluco pyranosyl, as well as processes for preparing them. The preparation process consists of reacting the 5-hydroxy-psoralene or bergaptol with a monohalide of formula R—Hal in which R is defined as hereinbefore, in the presence of sodium hydride, preferably at ambient temperature, accompanied by vigorous stirring and cooling, preferably for 40 to 48 hours. The product obtained is then recovered, preferably by being poured onto crushed ice, suction-filtered and washed several times with cold water, dried and recrystallised in an ethanol-water mixture (50:50). The preferred halides are chlorides and bromides.

The processes and compounds of the present invention are illustrated in the Examples which follow:

EXAMPLE 1

5-Methoxy-psoralene was produced as set forth in the second paragraph of the Summary of the Invention.

The 5-methoxy-psoralene or bergaptene obtained is a light grey colour but is chemically pure. It has the following percentage analysis:

|  | calculated | found |
|---|---|---|
| Carbon % | 66.67 | 66.83 |
|  | 3.73 | 3.97 |
|  | 29.60 | 29.41 |

After recrystallising in hot ethanol, it is obtained in the form of fine pearly needles with a melting point of $193°$ C. with the same percentage analysis.

Thin layer chromatography with silica gel Merck 1500 LS-254 and ethanol/benzene:3/27 as solvents gives Rf=0.63.

EXAMPLE 2

Preparation of 5-hydroxy-psoralene or bergaptol

Reaction:

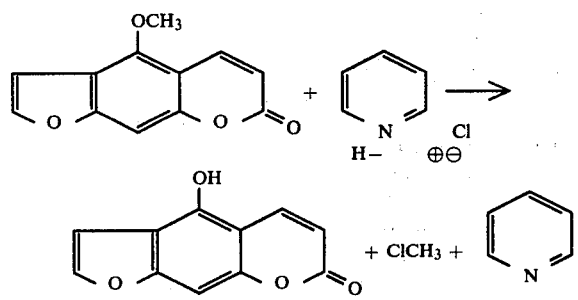

Operating procedure

A mixture of one part of 5-methoxy-psoralene or bergaptene and 3 to 10 parts of pyridinium chloride (purified and absolutely anhydrous) are heated at between 170° and 190° C. for a period of 1 to 4 hours accompanied by constant stirring in a three-necked flask equipped with a reflux condenser terminated by a calcium chloride guard, an internal thermometer and a mechanical or magnetic stirrer.

During heating samples of the reaction mass are taken and the kinetics of this demethylation process are followed until all the bergaptene has been demethylated.

Treatment

The complete mixture is poured onto crushed ice, dried, washed several times with cold water, dried in air or in a dessicator and recrystallised in absolute ethanol (without optional decolourisation by carbon-black). Average yield (over 10 tests): 72 to 85%.

The 5-hydroxy-psoralene obtained is in the form of fine yellow crystals, m.p. 275° C.

| Molecular weight: 202.17 | | |
|---|---|---|
| Percentage analysis: | calculated | found |
| Carbon % | 65.36 | 65.32 |
| Hydrogen % | 2.99 | 3.24 |
| Oxygen % | 31.65 | 31.60 |
| Thin-layer chromatography TLC | | |
| Silica gel Merck F-1500 LS - 254 | | |
| Solvents: Ethanol/benzene (3/27) | | |
| Rf = 0.25 | | |
| FeCl$_3$ test: positive, revealing the presence of an OH group. | | |

EXAMPLE 3 n-Decanoyl-5-oxy-psoralene

The preparation reaction is as follows:

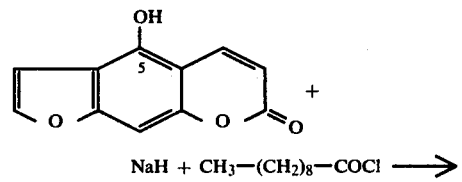

NaH + CH$_3$—(CH$_2$)$_8$—COCl ⟶

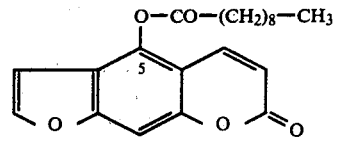

Operating procedure

A mixture of 30 ml of pure anhydrous DMF (dimethyl-formamide), 1.01 g (or 5 mM) of bergaptol of molecular weight 202, 1 g (or 5 mM with a slight excess of 6%) of freshly rectified n-decanoyl chloride of molecular weight 190.5 and 0.15 g (or 5 mM with 25% excess) of sodium hydride of molecular weight 24 is stirred vigorously at ambient temperature in the laboratory for 48 hours in an Erlenmeyer flask or a flat-bottomed flask equipped with an air condenser and terminated by a calcium chloride guard.

It is poured onto crushed ice, the precipitate formed is filtered or suction-filtered, dried and recrystallised in an ethanol-water mixture.

Yield: 1.26 g i.e. approximately 70%

The n-decanoyl-5-oxy-psoralene obtained was studied and defined by the following physico-chemical characteristics:

| Empirical formula: C$_{21}$H$_{24}$O$_5$ | | |
|---|---|---|
| Molecular weight: 356.41 | | |
| Percentage analysis: | calculated | found |
| Carbon % | 70.85 | 70.67–70.32 |
| Hydrogen % | 6.80 | 7.03–7.16 |

Characteristics: Fine colourless crystals or very fine colourless needles, m.p. 79° C.

Insoluble in water.

Soluble in alcohols, glycols and vegetable oils.

TLC: Merck F-1500 LS-254

Solvents: Cyclohexane/absolute ethanol: 30/5

Rf=0.80

Fe Cl$_3$ test: Negative

The remarkable feature of this psoralene derivative is that it is lipo-soluble.

EXAMPLE 4

(Ortho-acetoxy)-benzoyl-5-oxy-psoralene

The preparation reaction is as follows:

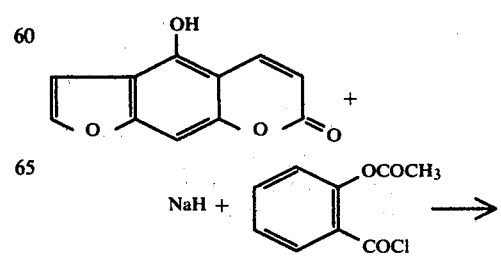

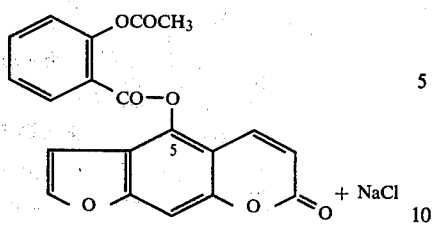

Operating procedure

The same apparatus is used as indicated hereinbefore. 300 mg or 1.4 mM (with a very slight excess) of bergaptol of molecular weight 202 are dissolved into 10 ml of pure anhydrous DMF. Accompanied by vigorous stirring 42 mg or 1.4 mM (with a 25% excess) of sodium hydride with a molecular weight of 24 are introduced. When the solution becomes homogeneous, a solution of 260 mg of 1.4 mM (with a slight excess) of freshly rectified ortho-acetoxy-benzoyl chloride in 5 ml of pure anhydrous DMF are added in five small fractions.

A very definite reaction occurs on each addition and the colour changes from orange-yellow to light yellow. Stirring is continued for 40 hours.

It is poured onto crushed ice, the precipitate is suction-filtered, washed several times with cold water, dried and recrystallised in an ethanol-water mixture (50:50).

Yield: 330 mg, i.e. approximately 65%.

The (ortho-acetoxy)-benzoyl-5-oxy-psoralene or psoralene aspirinate obtained was studied and is defined by the following physicochemical characteristics:

Empirical formula: $C_{20}H_{12}O_7$
Molecular weight: 364

| Percentage analysis: | calculated | found |
|---|---|---|
| Carbon % | 66.00 | 66.09 |
| Hydrogen % | 3.32 | 3.43 |
| Oxygen % | 30.77 | 30.63 |

CHARACTERISTICS:

Colourless fine crystals, m.p. 149°–151° C., soluble hot in ethanol.
TLC: Silica gel Merck F 1500 LS-254
Solvents: Benzene/ethyl acetate: 80/20, Rf=0.64
Fe Cl₃ test: Negative

EXAMPLE 5

α-Thenoyl-5-oxy-psoralene

The preparation reaction is as follows:

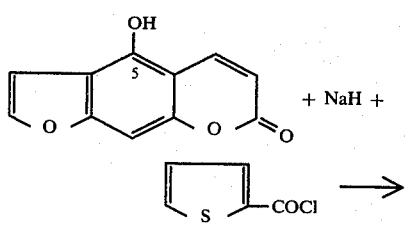

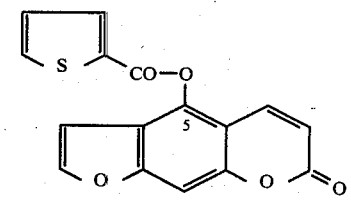

Operating procedure

The same equipment as used hereinbefore is employed. A mixture of 30 ml of pure anhydrous DMF, 1.01 g (or 5 mM) of bergaptol of molecular weight 202, 0.80 g (or 5 mM)(with a slight excess) of α-thenoylchloride of molecular weight 146.5 and 0.15 g (or 6 mM with a slight excess) of sodium hydride of molecular weight 24, is kept at ambient temperature for 48 hours accompanied by figorous stirring.

It is poured onto crushed ice, the precipitate is suction-filtered, dried and recrystallised in hot ethanol.

Yield: 1.05 g, i.e. approximatly 70% of the theoretical yield. α-Thenoyl-5-oxy-psoralene or "sulphur psoralene" was studied and defined by the following physico-chemical characteristics:

Empirical formula: $C_{16}H_7O_5S$
Molecular weight: 311.30

| Percentage analysis: | calculated | found |
|---|---|---|
| Carbon % | 61.79 | 61.55–61.65 |
| Hydrogen % | 2.26 | 2.60–2.63 |
| Oxygen % | 25.72 | 25.70–25.65 |
| Sulphur % | 10.31 | 10.21–10.09 |

Physico-chemical characteristics

Fine yellow crystals, m.p. = 198° C., insoluble in water, soluble in ethanol (hot).
TLC: Silica gel Schleider-Schüll F-1500 LS-254
Solvents: Benzene/methanol: 27/3, Rf=0.69
FeCl₃ test: Negative

EXAMPLE 6

β-Diethyl-amino-5-ethoxy-psoralene

The preparation reaction is as follows:

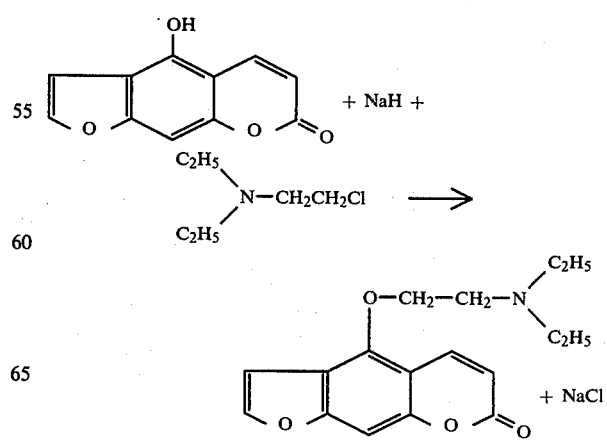

Operating procedure

Into an Erlenmeyer of flat-bottomed flask equipped with an air reflux condenser (terminated by a calcium chloride guard) are successively introduced, accompanied by vigorous magnetic stirring 50 ml of pure anhydrous DMF, 2.02 g (or 10 mM) of bergaptol of molecular weight 202, and 0.30 g (or 12.5 mM)(with a 25% excess) of sodium hydride of molecular weight 24, and then dropwise a solution of 2 g (or 15 mM with a 50% excess) of β-diethylamino-ethyl chloride (in the form of a base, freshly obtained from the corresponding hydrochloride and rectified) of molecular weight 131.5 in 10 ml of anhydrous DMF.

After stirring for 50 hours at ambient temperature, the reaction mass is poured into 100 ml of cold water and acidified with concentrated hydrochloric acid to pH 3 in order to dissolve all the hydrochloride from the sought product. The organic impurities are eliminated by extracting three times on each occasion with 30 ml of benzene.

Alkalisation with concentrated ammonia to a pH of 10 is carried out in order to free the sought base which is extracted four times with on each occasion 50 ml of benzene. The benzene solutions are combined and washed with 30 ml of cold water. Drying takes place on anhydrous sodium sulphate, followed by filtering, expulsion of the excess solvent and collection of the pale yellow crystals. They are recrystallised in absolute ethanol accompanied by decolourisation with carbon-black.

Fine colourless crystals, m.p. 76°–77° C.

Yield: 2.40 g, i.e. approximately 80% compared with the theoretical yield.

HYDROCHLORIDE 1 g of base (constituted by fine colourless crystals) is dissolved in 50 ml of anhydrous sulphuric ether. A solution of anhydrous sulphuric ether saturated with gaseous hydrochloric acid is then added in small fractions until maximum precipitation of the sought hydrochloride is obtained. Rapid suction-filtering takes place followed by washing with anhydrous ether.

Yield: Quantitative in hydrochloride (compared with the base).

β-Diethyl-amino-5-ethoxy-psoralene hydrochloride was studied and defined by the following physico-chemical characteristics:

Empirical formula: $C_{17}H_{19}NO_4$, HCl
Molecular weight: 337.5

| Percentage analysis: | calculated | found |
|---|---|---|
| Carbon % | 60.59 | 59.71 |
| Hydrogen % | 5.68 | 6.11 |
| Nitrogen % | 4.16 | 3.88 |
| Oxygen % | 18.99 | 19.30 |
| Chlorine % | 10.52 | 10.87 |

Characteristics

Fine colourless crystals, m.p. 230° C.
Soluble in water
Soluble hot in ethanol.
TLC: Silica gel Merck F 1500 LS-254
Solvents: Benzene/ethyl acetate/ethanol/ammonia: 21/6/4/0.5
Rf=0.31

Fe Cl$_3$ test: Negative

The surprising feature of this psoralene derivative is that it is hydro-soluble.

EXAMPLE 7

(O,O-diethyl-phosphino)-5-oxy-psoralene

The preparation reaction is as follows:

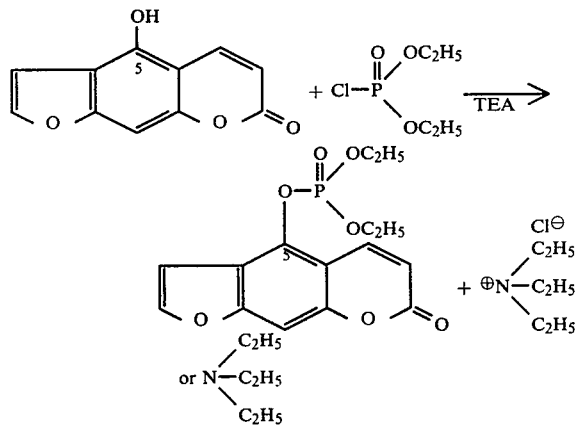

Operating procedure

The same equipment is used as described hereinbefore. 500 mg (or 2.5 mM) of bergaptol of molecular weight 202, 20 ml of pure ahydrous DMF, 500 mg (or 5 mM) of TEA or pure anhydrous triethyl-amine of molecular weight 101 (weight absorbs the hydrochloric acid given off during the reaction) and 483 mg (or 2.8 mM) of diethyl-chlorophosphate (freshly rectified) of molecular weight 172.5 dissolved in 10 ml of pure anhydrous DMF are vigorously stirred for 8 hours at ambient temperature.

The excess DMF and triethyl-amine are expelled under high vacuum and preferably at ambient temperature.

The residue thereof is taken up in 40 ml of chloroform. The chloroformic solution is washed with ice water, then several times with a 5% sodium bicarbonate solution up to neutrality of the washing waters. A final washing operation takes place with ice water.

Drying takes place on anhydrous magnesium sulphate, followed by filtering and the expulsion of the excess chloroform.

The residue is taken up in anhydrous ether and fine pink crystals are obtained. Recrystallisation takes place in absolute ethanol giving fine colourless crystals.

Yield: 465 mg, i.e. approximately 55% of theory.

(O,O-diethyl-phosphone)-5-oxy-psoralene or diethyl-furocoumarin or phosphorylated psoralene was studied and defined by the following physico-chemical characteristics:

Empirical formula: $C_{15}H_{14}O_7P$
Molecular weight: 337.25

| Percentage analysis: | calculated | found |
|---|---|---|
| Carbon % | 53.46 | 53.38–53.30 |
| Hydrogen % | 4.32 | 4.52 |
| Phosphorus % | 9.19 | 9.28–9.52 |
| Oxygen % | 33.23 | |

Characteristics

Fine colourless crystals, m.p. 99°–100° C.
Soluble hot in alcohols
TLC: Silica gel Merck F 1500 LS-254
Solvents: Benzene/ethyl acetate/ethanol: 21/6/4
Rf=0.67
$FeCl_3$ test: Negative

EXAMPLE 8

Tetra-2′,3′,4′,6′-α-acetyl,
D-gluco-pyranosyl-5-oxy-psoralene

The preparation reaction was as follows:

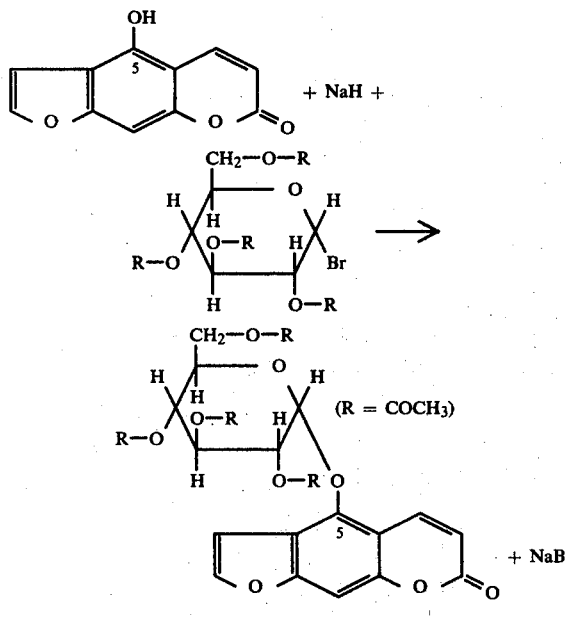

Operating procedure

Same apparatus as previously used.

606 mg (or 3 mM) of bergaptol of molecular weight 202 were dissolved cold accompanied by powerful magnetic stirring in 20 ml of pure anhydrous DMF, followed by the addition of 85 mg (or 3.2 mM) of sodium hydride, stirring being maintained until a clear solution was obtained.

A solution of 1.32 g (or 3.2 mM) of acetobromoglucose dissolved in 10 ml of anhydrous DMF (molecular weight 411), was then introduced. Stirring was maintained for 2 hours. The reaction mass was poured into 150 ml of cold water.

A few hours later a light yellow precipitate was obtained which was suction-filtered and recrystallized in absolute ethanol Yield: 720 mg of fine yellow crystals, i.e. approximately 45% of theory.

Tetra-2′,3′,4′,6′-α-acetyl, D-gluco-pyranosyl-5-oxy-psoralene or "gluco-psoralene" was studied and defined by the following physicochemical characteristics:

Empirical formula: $C_{25}H_{24}O_{13}$
Molecular weight: 532.38

| Percentage analysis: | calculated | found |
|---|---|---|
| Carbon % | 56.39 | 55.98–55.96 |
| Hydrogen % | 4.55 | 4.85–4.80 |
| Oyxgen % | 39.06 | 39.28–39.32 |

Characteristics

Fine yellow crystals, m.p. 126°–128° C., moderately soluble in water, soluble in ethanol (hot).
TLC: Silica gel F—1500 LS-254
Solvents: Benzene/ethanol: 30/10, Rf=0.73
$FeCl_3$ test: Negative.

All novel derivatives of psoralene prepared according to the process of this invention can be used in therapeutical treatments of dermatological diseases.

I claim:

1. RO substituted psoralenes of the formula

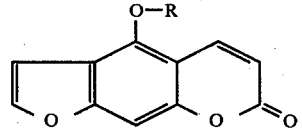

wherein R is a radical selected from the group consisting of alkanoyl of not more than 10 carbon atoms, ortho-acetoxy-benzoyl, α thenoyl O,O diethyl-phosphono, diethylaminoethyl, and 2′3′4′6′ tetra α acetyl D-gluco pyranosyl.

2. A compound according to claim 1 which is n-decanoyl-5-oxy-psoralene.

3. A compound according to claim 1 which is (ortho-acetoxy)-benzoyl-5-oxy-psoralene.

4. A compound according to claim 1 which is β-diethyl-amino-5-ethoxy-psoralene.

5. A compound according to claim 1 which is β-diethyl-amino-5-ethoxy-psoralene hydrochloride.

6. A compound according to clai 1 which is (O,O-diethyl-phosphono)-5-oxy-psoralene.

7. A compound according to claim 1 which is 2′3′4′6′ tetra α acetyl D-gluco-pyranosyl-5-oxy-psoralene.

8. A compound according to claim 1 which is α-thenoyl-5-oxy-psoralene.

* * * * *